United States Patent
Yoshida

(10) Patent No.: US 8,226,623 B2
(45) Date of Patent: Jul. 24, 2012

(54) SPREAD OUT-TYPE PAPER DIAPER

(75) Inventor: Hideaki Yoshida, Tochigi (JP)

(73) Assignee: Daio Paper Corporation, Ehime (JP)

( * ) Notice: Subject to any disclaimer, the term of this patent is extended or adjusted under 35 U.S.C. 154(b) by 910 days.

(21) Appl. No.: 10/594,663

(22) PCT Filed: Mar. 30, 2005

(86) PCT No.: PCT/JP2005/006078
§ 371 (c)(1),
(2), (4) Date: May 12, 2008

(87) PCT Pub. No.: WO2005/094750
PCT Pub. Date: Oct. 13, 2005

(65) Prior Publication Data
US 2009/0018519 A1    Jan. 15, 2009

(30) Foreign Application Priority Data

Mar. 30, 2004    (JP) .................. 2004-099412

(51) Int. Cl.
*A61F 13/15* (2006.01)
*A61F 13/20* (2006.01)
(52) U.S. Cl. ........ 604/385.01; 604/385.19; 604/385.101
(58) Field of Classification Search .............. 604/385.01, 604/385.16, 385.19, 385.22, 385.24, 385.27–385.29
See application file for complete search history.

(56) References Cited

U.S. PATENT DOCUMENTS

| 5,897,544 | A | * | 4/1999 | Ronnberg | 604/385.19 |
| 7,238,175 | B2 | * | 7/2007 | Onishi et al. | 604/385.24 |

FOREIGN PATENT DOCUMENTS

| JP | 6-005614 | 1/1994 |
| JP | 8-196565 | 8/1996 |
| JP | 2002-325795 | 11/2002 |
| JP | 2004-008301 | 1/2004 |

* cited by examiner

*Primary Examiner* — Michele M Kidwell
(74) *Attorney, Agent, or Firm* — Jordan and Hamburg LLP

(57) ABSTRACT

A comfortably wearable development type paper diaper comprises a back sheet, a first absorbent, a second absorbent and a liquid-permeable top sheet in the recited order. The first absorbent extends, when worn, from the back side through the crotch to the abdomen side of the user. The second absorbent extends, when worn, from the back side to the crotch of the user. A leakage preventing sheet allowing no liquid permeation is interposed between the first absorbent and the second absorbent. The second absorbent leaves the first absorbent from the crotch to the back side thereby to form a pocket PO for holding the excrement between the first absorbent and the second absorbent. The leakage preventing sheet is arranged to contact in the pocket PO with the second absorbent. The top sheet is so conformed to the shape of the pocket PO as to cover the leakage preventing sheet.

4 Claims, 14 Drawing Sheets

SPREAD OUT-TYPE PAPER DIAPER

BACKGROUND OF THE INVENTION

The present invention relates to a development type paper diaper which is worn on a human body for absorbing and holding excrements.

In the development type paper diaper of the prior art, a holding portion for holding the feces is disposed at the portion where the buttocks of the user are positioned. In this paper diaper, a recess is so formed in an absorbent as to have its opening covered planarly with a top sheet, or the top sheet is disposed along the shape of the recess. In such a portion of the top sheet covering the opening of the recess of the absorbent planarly as overlaps the opening, there is formed a hole, from which the feces is guided into the recess of the absorbent and is held (as referred to Patent Document 1, for example).

However, this development type paper diaper has to retain the recessed shape formed in the absorbent thereby to hold the feces. This raises a problem that the inner wall of the recess has to be solidified or covered with a strong liquid-permeable sheet in place of the surface sheet.

Thus, there has been disclosed (in Patent Document 2, for example) a development type paper diaper, as shown in FIG. 14. This paper diaper includes a back sheet 1, a first absorbent (or a lower-layer absorbent) 2, a second absorbent (or an upper-layer absorbent) 3 and a top sheet 4 in the recited order. The second absorbent 3 is composed of a front side portion 3a and a rear side portion 3b, which divide the second absorbent 3 into front and rear halves at the portion abutting against the buttocks. The rear end of the front side portion 3a and the front end of the rear side portion 3b are spaced at a predetermined distance in the longitudinal direction. The top sheet 4 is folded toward the first absorbent 2 at the rear end of the front side portion 3a and the front end of the rear side portion 3b. This bent portion is formed into a pocket 5, which is folded between the first absorbent 2 and the second absorbent 3 thereby to hold the feces.

Patent Document 1: JP-UM-A-6-5614
Patent Document 2: Japanese Patent No. 3,130,438

However, some user of the development type paper diaper is left long in bed and has decubitus on the waist. This decubitus is accompanied by physical and metal pains, and is thought to occur due to the bloodstream inhibition, the reductions in the metabolism, natural purification and immunity, and/or the physical frictions at the body position change. However, more serious causes for the decubitus are that the skin is contaminated to have a rash by the moisture contained in the excrements.

The development type paper diaper having the constitutions shown in FIG. 6 has found it difficult to avoid the aforementioned causes. This is because the excrement held in the pocket 5 permeates into the second absorbent 3 and contacts and contaminates the skins of the buttocks and waists of the user through the top sheet 4, so that the decubitus cannot be prevented from advancing.

Thus, an object of this invention is to provide a development type paper diaper which can be comfortably worn by the user.

SUMMARY OF THE INVENTION

According to a first aspect of the invention, therefore, there is provided a development type paper diaper adapted to be worn on a human body for absorbing and holding excrements, comprising a back sheet, a first absorbent, a second absorbent and a top sheet in the recited order, characterized: in that the first absorbent extends, when worn, from the back side through the crotch to the abdomen side of the user; in that the second absorbent extends, when worn, from the back side to the crotch of the user; in that a leakage preventing sheet allowing no liquid permeation is interposed between the first absorbent and the second absorbent; in that the second absorbent leaves the first absorbent from the crotch to the back side thereby to form a pocket for holding the excrement between the first absorbent and the second absorbent; in that the leakage preventing sheet is arranged to contact in the pocket with the second absorbent; and in that the top sheet is so conformed to the shape of the pocket as to cover the leakage preventing sheet.

According to a second aspect of the invention, there is provided a development type paper diaper adapted to be worn on a human body for absorbing and holding excrements, comprising a back sheet, a first absorbent, a second absorbent and a top sheet in the recited order, characterized: in that the first absorbent extends, when worn, from the back side through the crotch to the abdomen side of the user; in that the second absorbent extends, when worn, from the crotch to the abdomen side of the user; in that a leakage preventing sheet allowing no liquid permeation is interposed between the first absorbent and the second absorbent; in that the second absorbent leaves the first absorbent from the crotch to the abdomen side thereby to form a pocket for holding the excrement between the first absorbent and the second absorbent; in that the leakage preventing sheet is arranged to contact in the pocket with the second absorbent; and in that the top sheet is so conformed to the shape of the pocket as to cover the leakage preventing sheet.

According to a third aspect of the invention, there is provided a development type paper diaper adapted to be worn on a human body for absorbing and holding excrements, comprising a back sheet, a first absorbent, a second absorbent and a top sheet in the recited order, characterized: in that the first absorbent extends, when worn, from the back side through the crotch to the abdomen side of the user; in that the second absorbent includes a back side second absorbent extending, when worn, from the back side to the crotch of the user and an abdomen side second absorbent extending, when worn, from the crotch to the abdomen side of the user; in that a leakage preventing sheet allowing no liquid permeation is interposed individually between the first absorbent and the back side second absorbent and between the first absorbent and the abdomen side second absorbent; in that the back side second absorbent leaves the first absorbent from the crotch to the back side, and the abdomen side second absorbent leaves the first absorbent from the crotch to the abdomen side, thereby to form pockets for holding the excrement individually between the first absorbent and the back side second absorbent and between the first absorbent and the abdomen side second absorbent; in that the leakage preventing sheet is arranged to contact in the pocket with the back side second absorbent or the abdomen side second absorbent; and in that the top sheet is so conformed to the shape of the pocket as to cover the leakage preventing sheet.

In a development type paper diaper as set forth in any of the first to third aspects of the invention, according to a fourth aspect of the invention, an excrement containing gathering is disposed along the opening upper end of the pocket and on the top sheet of the second absorbent.

According to a fifth aspect of the invention of, there is provided a development type paper diaper adapted to be worn on a human body for absorbing and holding excrements, comprising a back sheet, a first absorbent, a second absorbent, a third absorbent and a top sheet in the recited order, characterized: in that the first absorbent extends, when worn, from the back side through the crotch to the abdomen side of the user; in that the second absorbent and the third absorbent extend, when worn, from the back side to the crotch of the user; in that a leakage preventing sheet allowing no liquid permeation is interposed between the second absorbent and the third absorbent; in that the second absorbent leaves the first absorbent from the crotch to the back side thereby to form a pocket for holding the excrement between the first absorbent and the second absorbent; and in that the top sheet is conformed to the shape of the pocket.

According to a sixth aspect of the invention, there is provided a development type paper diaper adapted to be worn on a human body for absorbing and holding excrements, comprising a back sheet, a first absorbent, a second absorbent, a third absorbent and a top sheet in the recited order, characterized: in that the first absorbent extends, when worn, from the back side through the crotch to the abdomen side of the user; in that the second absorbent and the third absorbent extend, when worn, from the crotch to the abdomen side of the user; in that a leakage preventing sheet allowing no liquid permeation is interposed between the second absorbent and the third absorbent; in that the second absorbent leaves the first absorbent from the crotch to the abdomen side thereby to form a pocket for holding the excrement between the first absorbent and the second absorbent; and in that the top sheet is conformed to the shape of the pocket.

According to a seventh aspect of the invention, there is provided a development type paper diaper adapted to be worn on a human body for absorbing and holding excrements, comprising a back sheet, a first absorbent, a second absorbent, a third absorbent and a top sheet in the recited order, characterized: in that the first absorbent extends, when worn, from the back side through the crotch to the abdomen side of the user; in that the second absorbent includes a back side second absorbent extending, when worn, from the back side to the crotch of the user, and an abdomen side second absorbent extending, when worn, from the back side to the crotch of the user; in that the third absorbent includes a back side third absorbent extending, when worn, from the back side to the crotch of the user, and an abdomen side third absorbent extending, when worn, from the back side to the crotch of the user; in that a leakage preventing sheet allowing no liquid permeation is interposed between the back side second absorbent and the back side third absorbent and between the abdomen side second absorbent and the abdomen side third absorbent; in that the back side second absorbent leaves the first absorbent from the crotch to the back side, and the abdomen side second absorbent leaves the first absorbent from the crotch to the abdomen side, thereby to form pockets for holding the excrement individually between the first absorbent and the back side second absorbent and between the first absorbent and the abdomen side second absorbent; and in that the top sheet is conformed to the shape of the pocket.

In a development type paper diaper as set forth in any of the fifth to seventh aspects of the invention, according to an eighth aspect of the invention, an excrement containing gathering is disposed along the opening of the pocket and on the top sheet of the second absorbent or the third absorbent.

In a development type paper diaper as set forth in any of the first to eight aspects of the invention, according to a ninth aspect of the invention, a cubic leg gathering is disposed along the first absorbent.

In a development type paper diaper as set forth in any of the first to ninth aspects of the invention, according to a tenth aspect of the invention, the first absorbent has a less amount at the widthwise center than that on the two sides in the widthwise direction.

According to the first aspect of the invention: the development type paper diaper comprises a back sheet, a first absorbent, a second absorbent and a top sheet in the recited order; the first absorbent extends, when worn, from the back side through the crotch to the abdomen side of the user; the second absorbent extends, when worn, from the back side to the crotch of the user; a leakage preventing sheet allowing no liquid permeation is interposed between the first absorbent and the second absorbent; the second absorbent leaves the first absorbent from the crotch to the back side thereby to form a pocket for holding the excrement between the first absorbent and the second absorbent; the leakage preventing sheet is arranged to contact in the pocket with the second absorbent; and the top sheet is so conformed to the shape of the pocket as to cover the leakage preventing sheet. As a result, the excrements are held in the pocket between the first absorbent and the second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the works of the care taker. In addition, the water content of the excrements held in the pocket is absorbed by and held in the first absorbent so that the water content does not flow back or leak out from the opening of the pocket.

Moreover, the leakage preventing sheet is so interposed between the first absorbent and the second absorbent as to contact with the second absorbent. As a result, the water content of the excrements held in the pocket is neither absorbed by the second absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be comfortably worn by the user.

According to the first aspect of the invention of claim 1: the development type paper diaper comprises a back sheet, a first absorbent, a second absorbent and a top sheet in the recited order; the first absorbent extends, when worn, from the back side through the crotch to the abdomen side of the user; the second absorbent extends, when worn, from the crotch 37 to the abdomen side of the user; a leakage preventing sheet allowing no liquid permeation is interposed between the first absorbent and the second absorbent; the second absorbent leaves the first absorbent from the crotch to the abdomen side thereby to form a pocket for holding the excrement between the first absorbent and the second absorbent; the leakage preventing sheet is arranged to contact in the pocket with the second absorbent; and the top sheet is so conformed to the shape of the pocket as to cover the leakage preventing sheet. As a result, the excrements are held in the pocket between the first absorbent and the second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the task of the care taker. In addition, the water content of the excrements held in the pocket is absorbed by and held in the first absorbent so that the water content does not flow back or leak out from the opening of the pocket.

Moreover, the leakage preventing sheet is so interposed between the first absorbent and the second absorbent as to contact with the second absorbent. As a result, the water content of the excrements held in the pocket is neither absorbed by the second absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be comfortably worn by the user.

According to the third aspect of the invention: the development type paper diaper comprises a back sheet, a first absorbent, a second absorbent and a top sheet in the recited order; the first absorbent extends, when worn, from the back side through the crotch to the abdomen side of the user; the second absorbent includes a back side second absorbent extending, when worn, from the back side to the crotch of the user and an abdomen side second absorbent extending, when worn, from the crotch to the abdomen side of the user; a leakage preventing sheet allowing no liquid permeation is interposed individually between the first absorbent and the back side second absorbent and between the first absorbent and the abdomen side second absorbent; the back side second absorbent leaves the first absorbent from the crotch to the back side, and the abdomen side second absorbent leaves the first absorbent from the crotch to the abdomen side, thereby to form pockets for holding the excrement individually between the first absorbent and the back side second absorbent and between the first absorbent and the abdomen side second absorbent; the leakage preventing sheet is arranged to contact in the pocket with the back side second absorbent or the abdomen side second absorbent; and the top sheet is so conformed to the shape of the pocket as to cover the leakage preventing sheet. As a result, the excrements are held individually in the pocket formed between the first absorbent and the back side second absorbent and in the pocket formed between the first absorbent and the abdomen side second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the task of the care taker. In addition, the water content of the excrements held in the pocket is absorbed by and held in the first absorbent so that the water content does not flow back or leak out from the opening of the pocket.

Moreover, the leakage preventing sheet is so interposed between the first absorbent and the back side second absorbent as to contact with the back side second absorbent, and the leakage preventing sheet is so interposed between the first absorbent and the abdomen side second absorbent as to contact with the abdomen side second absorbent. As a result, the water content of the excrements held in the pocket is neither absorbed by the back side second absorbent or the abdomen side second absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be comfortably worn by the user.

According to the fourth aspect of the invention, an excrement containing gathering is disposed along the opening upper end of the pocket and on the top sheet of the second absorbent. By the elastic member belonging to the excrement containing gathering, the second absorbent can be bent to form the opening of the pocket easily thereby to exploit the pocket effectively. As a result, the excrements can be easily held in the pocket, and the skin of the user can be kept clean without being contaminated by the excrements. Thus, it is possible to provide a development type paper diaper which can be comfortably worn by the user.

According to the fifth aspect of the invention: the development type paper diaper comprises a back sheet, a first absorbent, a second absorbent, a third absorbent and a top sheet in the recited order; the first absorbent extends, when worn, from the back side through the crotch to the abdomen side of the user; the second absorbent and the third absorbent extend, when worn, from the back side to the crotch of the user; a leakage preventing sheet allowing no liquid permeation is interposed between the second absorbent and the third absorbent; the second absorbent leaves the first absorbent from the crotch to the back side thereby to form a pocket for holding the excrement between the first absorbent and the second absorbent; and the top sheet is conformed to the shape of the pocket. As a result, the excrements are held in the pocket between the first absorbent and the second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the task of the care taker. In addition, the water content of the excrements held in the pocket is absorbed by and held not only in the first absorbent but also in the second absorbent so that the water content does not flow back or leak out from the opening of the pocket.

Moreover, the leakage preventing sheet is interposed between the second absorbent and the third absorbent as to contact with the second absorbent. As a result, the water content of the excrements held in the pocket is neither absorbed by the third absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be further comfortably worn by the user.

According to the sixth aspect of the invention: the development type paper diaper comprises a back sheet, a first absorbent, a second absorbent, a third absorbent and a top sheet in the recited order; the first absorbent extends, when worn, from the back side through the crotch to the abdomen side of the user; the second absorbent and the third absorbent extend, when worn, from the crotch to the abdomen side of the user; a leakage preventing sheet allowing no liquid permeation is interposed between the second absorbent and the third absorbent; the second absorbent leaves the first absorbent from the crotch to the abdomen side thereby to form a pocket for holding the excrement between the first absorbent and the second absorbent; and the top sheet is conformed to the shape of the pocket. As a result, the excrements are held in the pocket between the first absorbent and the second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the task of the care taker. In addition, the water content of the excrements held in the pocket is absorbed by and held not only in the first absorbent but also in the second absorbent so that the water content does not flow back or leak out from the opening of the pocket.

Moreover, the leakage preventing sheet is interposed between the second absorbent and the third absorbent. As a result, the water content of the excrements held in the pocket is neither absorbed by the third absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be further comfortably worn by the user.

According to the seventh aspect of the invention: the development type paper diaper comprises a back sheet, a first absorbent, a second absorbent, a third absorbent and a top sheet in the recited order; the first absorbent extends, when worn, from the back side through the crotch to the abdomen side of the user; the second absorbent includes a back side second absorbent extending, when worn, from the back side to the crotch of the user, and an abdomen side second absorbent extending, when worn, from the back side to the crotch of the user; the third absorbent includes a back side third absorbent extending, when worn, from the back side to the crotch of the user, and an abdomen side third absorbent extending, when worn, from the back side to the crotch of the user; a leakage preventing sheet allowing no liquid permeation is interposed between the back side second absorbent and the back side third absorbent and between the abdomen side second absorbent and the abdomen side third absorbent; the back side second absorbent leaves the first absorbent from the crotch to the back side, and the abdomen side second absorbent leaves the first absorbent from the crotch to the abdomen side, thereby to form pockets for holding the excrement individually between the first absorbent and the back side second absorbent and between the first absorbent and the abdomen side second absorbent; and the top sheet is conformed to the shape of the pocket. As a result, the excrements are held either in the pocket between the first absorbent and the back side second absorbent or in the pocket between the first absorbent and the abdomen side second absorbent, so that they do not expand all over the top sheet or the contact surface of the paper diaper thereby to keep the cleanness. At the time of replacing the development type paper diaper, moreover, the area for the care taker to wipe off the excrements of the user is decreased to reduce the task of the care taker. In addition, the water content of the excrements held in the pocket is absorbed by and held not only in the first absorbent but also in the second absorbent so that the water content does not flow back or leak out from the opening of the pocket.

Moreover, the leakage preventing sheet is interposed between the back side second absorbent and the back side third absorbent and between the abdomen side second absorbent and the abdomen side third absorbent. As a result, the water content of the excrements held in the pocket is neither absorbed by the back side third absorbent or the abdomen side third absorbent nor allowed to ooze out over the top sheet to the contact surface of the paper diaper. Even when the user is suffering from the decubitus, the paper diaper does not contaminate the affected part but keeps it clean. In addition, the affected part is not deteriorated by the excrements having been allowed to ooze out. Thus, it is possible to provide a development type paper diaper which can be further comfortably worn by the user.

According to the eighth aspect of the invention, an excrement containing gathering is disposed along the opening of the pocket and on the top sheet of the second absorbent or the third absorbent. By the elastic member belonging to the excrement containing gathering, the second absorbent or another second absorbent can be bent to form the opening of the pocket easily thereby to exploit the pocket effectively. As a result, the excrements can be easily held in the pocket, and the skin of the user can be kept clean without being contaminated by the excrements. Thus, it is possible to provide a development type paper diaper which can be comfortably worn by the user.

According to the ninth aspect of the invention, a cubic leg gathering is disposed along the first absorbent. Thus, it is possible to provide a development type paper diaper which can prevent the excrement from leaking sideways of the legs so that it can be comfortably worn by the user.

According to the tenth aspect of the invention, the first absorbent has a less amount at the widthwise center than that on the two sides in the widthwise direction. In case the first absorbent is made of a pulp, for example, a recess can be easily formed in the widthwise center of the first absorbent, so that the excrements can be easily guided to the center and further to the pocket thereby to keep the contact surface clean.

DETAILED DESCRIPTION OF THE INVENTION

A first mode of embodiment of this invention is described in the following with reference to the accompanying drawings.

Figure 1:
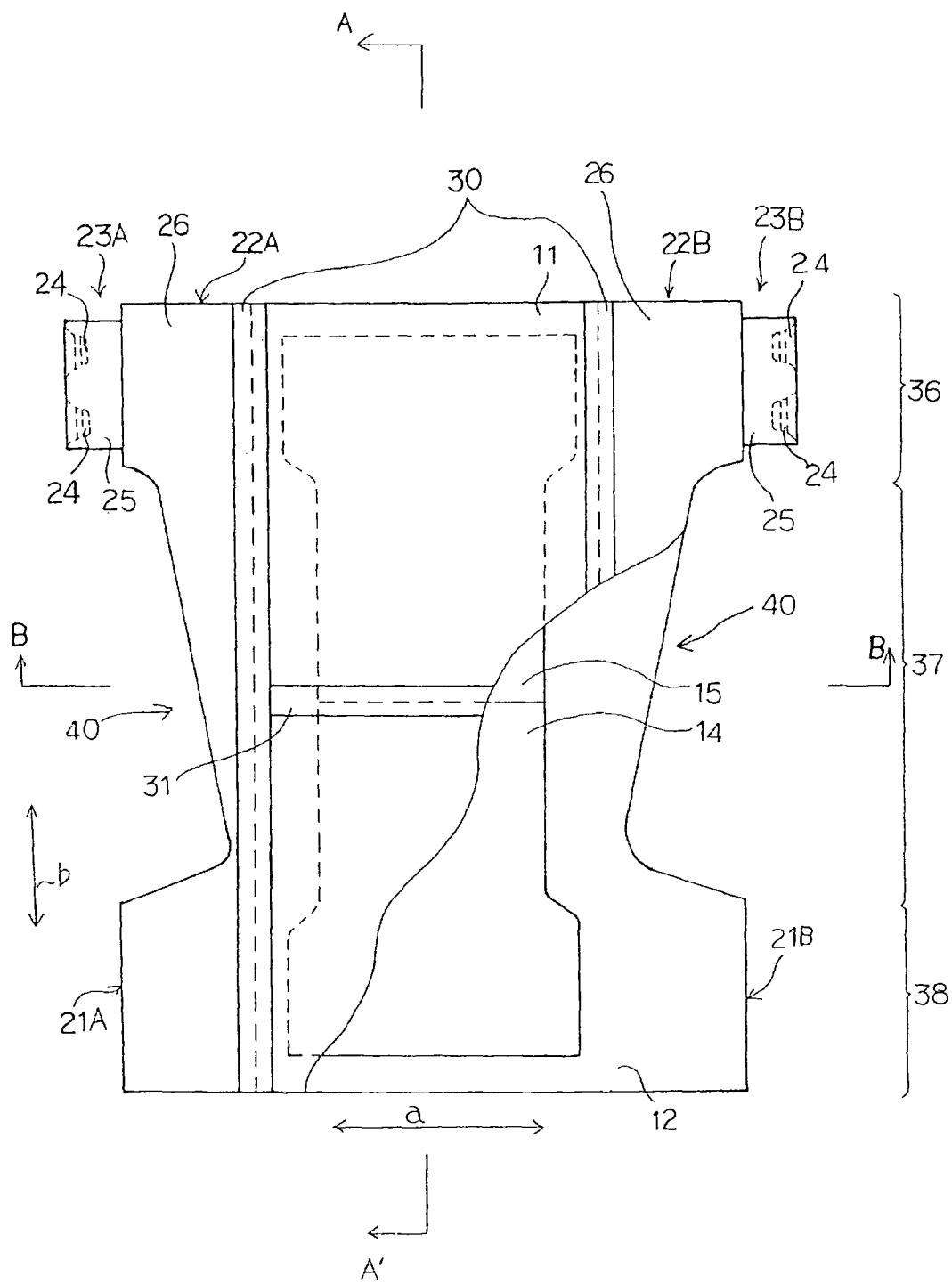
FIG. 1 is a top plan view of a development type paper diaper of a first mode of embodiment of this invention.

FIG. 1 is an expansion plan view of a development type paper diaper of this invention. This development type paper diaper is provided in the recited order with: a back sheet 12 of a rectangular shape having notches 40 formed generally at the central portions of the longer sides; a first absorbent (or a lower-layer absorbent) 14 extending at the center of the widthwise direction a of the back sheet 12 and in the longitudinal direction b; a second absorbent (or an upper-layer absorbent) 15 formed over the first absorbent 14; and a liquid-permeable top sheet 11 having a plurality of mesh holes and made of nonwoven fabric or film.

Figure 2:
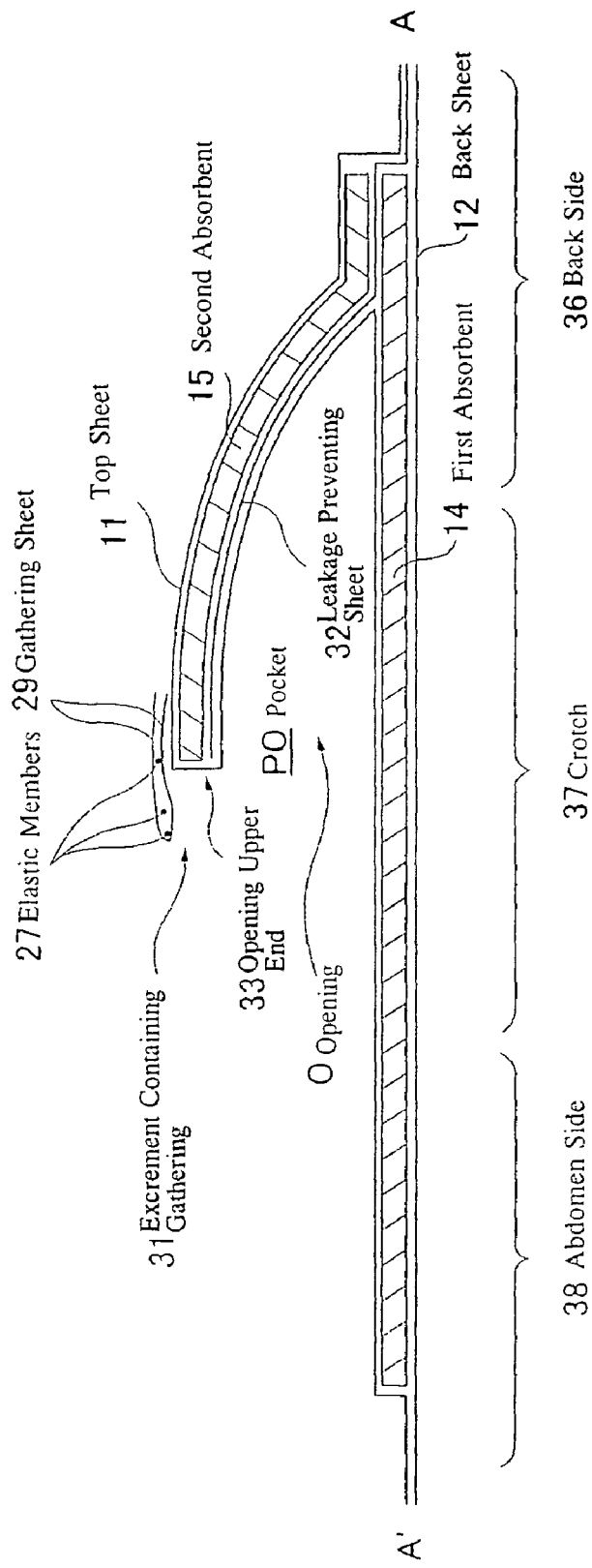
FIG. 2 is a section A-A' of the development type paper diaper of FIG. 1.
Figure 3:
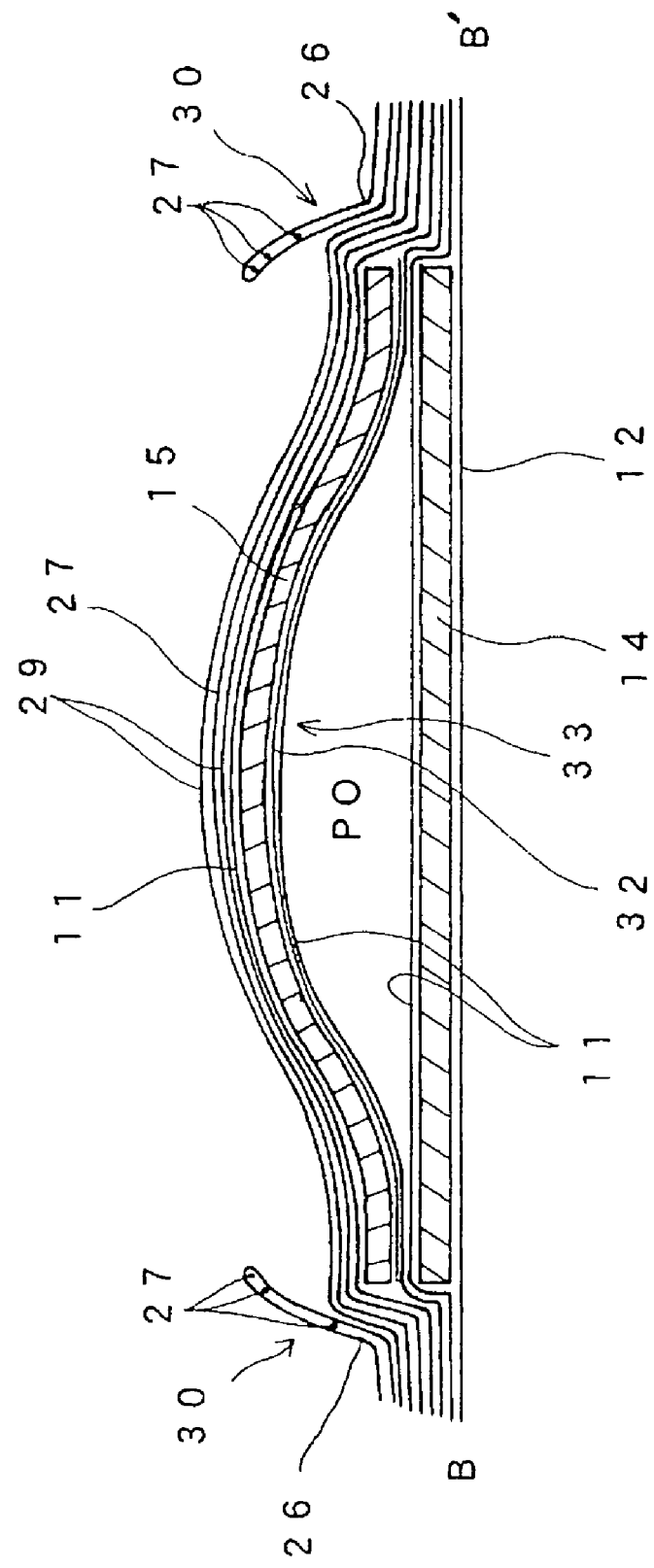
FIG. 3 is a section B-B' of the development type paper diaper of FIG. 1.

As shown in FIGS. 2 and 3, the first absorbent 14 is disposed, when worn, to extend from the back side 36 through the crotch 37 to the abdomen side 38 of the user, and the second absorbent 15 is disposed, when worn, to extend from the back side 36 to the crotch 37 of the user. A leakage preventing sheet 32 for allowing no liquid permeation is interposed between the first absorbent 14 and the second absorbent 15. The second absorbent 15 is spaced at its central portion from the first absorbent 14 as it goes from the crotch 37 to the back side 36 so that a pocket PO for holding the excrement is formed between the first absorbent 14 and the second absorbent 15. In that pocket PO, moreover, the leakage preventing sheet 32 is arranged to contact with the second absorbent 15, and the top sheet 11 is so conformed to the shape of the pocket PO as to cover the leakage preventing sheet 32.

At this time, the second absorbent 15 is adhered at its peripheral edge portion other than an opening O to the first absorbent 14 by means of a hot-melt adhesive.

Here, the top sheet 11 presents a using face when the development type paper diaper is worn on the user.

On the other hand, the first absorbent 14 and the second absorbent 15 are prepared by dispersing a high-molecular absorbent polymer in cotton-yarn pulp. Here, the first absorbent 14 and the second absorbent 15 are individually covered on their surfaces with absorbing tissue paper.

On the two sides of the back side 36 in the widthwise direction a, there are disposed a pair of side flaps 22A and 22B, respectively, which are provided on the outer sides in the widthwise direction a with side panels 23A and 23B having stopper portions 24.

These stopper portions 24 are integrally formed at the free end portion of a panel base 25, and each has a pinch portion at its leading end and an engagement portion such as a mechanical fastener acting as a male member at its stationary end. This engagement portion is fixed by adhering its back to the surface of the panel base 25.

A pair of side flaps 21A and 21B are formed on the two sides of the abdomen side 38 in the widthwise direction a.

Along the opening upper end 33 of the pocket PO, moreover, excrement containing gathering 31 is so adhered to the top sheet 11 over the second absorbent 15 that its leading end extends from the opening upper end 33 to the abdomen side 38.

This excrement containing gathering 31 is provided with three elastic members 27 along the widthwise direction a on the inner side by folding back a gathering sheet 29 formed of nonwoven fabric in the longitudinal direction b.

Here, the excrement containing gathering 31 may be so disposed along the opening upper end 33 of the pocket PO that its leading end is arranged either on that opening upper end 33 or on the back side 36.

In addition, a cubic leg gathering 30 is formed along the outer edge of the first absorbent 14 and along the longitudinal direction b.

This cubic leg gathering 30 is provided with the three elastic members 27 along the widthwise direction a on the inner side by folding back one end of a gathering sheet 26 formed of nonwoven fabric in the widthwise direction a.

In this drawing, the cubic leg gathering 30 and the excrement containing gathering 31 are individually provided with the three elastic members 27, to which the invention should not be limited. Moreover, the cubic leg gathering 30 fits, when the development type paper diaper is properly worn on the user, well around the legs of the user thereby to prevent the excrement from leaking sideways.

The other ends of the gathering sheets 26 are cut to correspond to the shapes of the side flaps 21A, 21B, 22A and 22B formed at the back sheet 12, and are adhered to the back sheet 12.

Here, the first absorbent 14 may be made of pulp in less amount at the center in the widthwise direction a than on the two sides of the widthwise direction a.

With this arrangement, the center of the first absorbent 14 in the widthwise direction a is more recessed than on the two sides so that it can gather the excrement at the center and can guide it easily to the pocket PO thereby to keep the using face clean.

When the development type paper diaper thus constituted is to be used, the user having face up lies at his or her buttocks on the top sheet 11 or the using face of the back side 36.

Then, the crotch 37 is applied to the crotch portion of the user, and the development type paper diaper is folded to place the abdomen side 38 on the abdomen of the user. The mechanical fasteners or the male members of the stopper portions 24 on the back side 36 are engaged with and fastened by the back sheet 12 of the abdomen side 38. Thus, the user wears the development type paper diaper. Then, the second absorbent 15 is raised to follow the body shape of the user by the excrement containing gathering 31 thereby to form the pocket PO.

If the excrement containing gathering 31 is closely worn on the vicinity of the sacrum portion of the user, the opening O of the pocket PO can catch the excrement of the user properly thereby to hold it easily in the pocket PO. If the amount of the pulp is made less at the center of the first absorbent 14 in the widthwise direction a than on the two sides in the widthwise direction a, the center of the first absorbent 14 in the widthwise direction a is more recessed than on the two sides so that the excrement can be gathered at the center and easily guided to the pocket PO.

Figure 4:
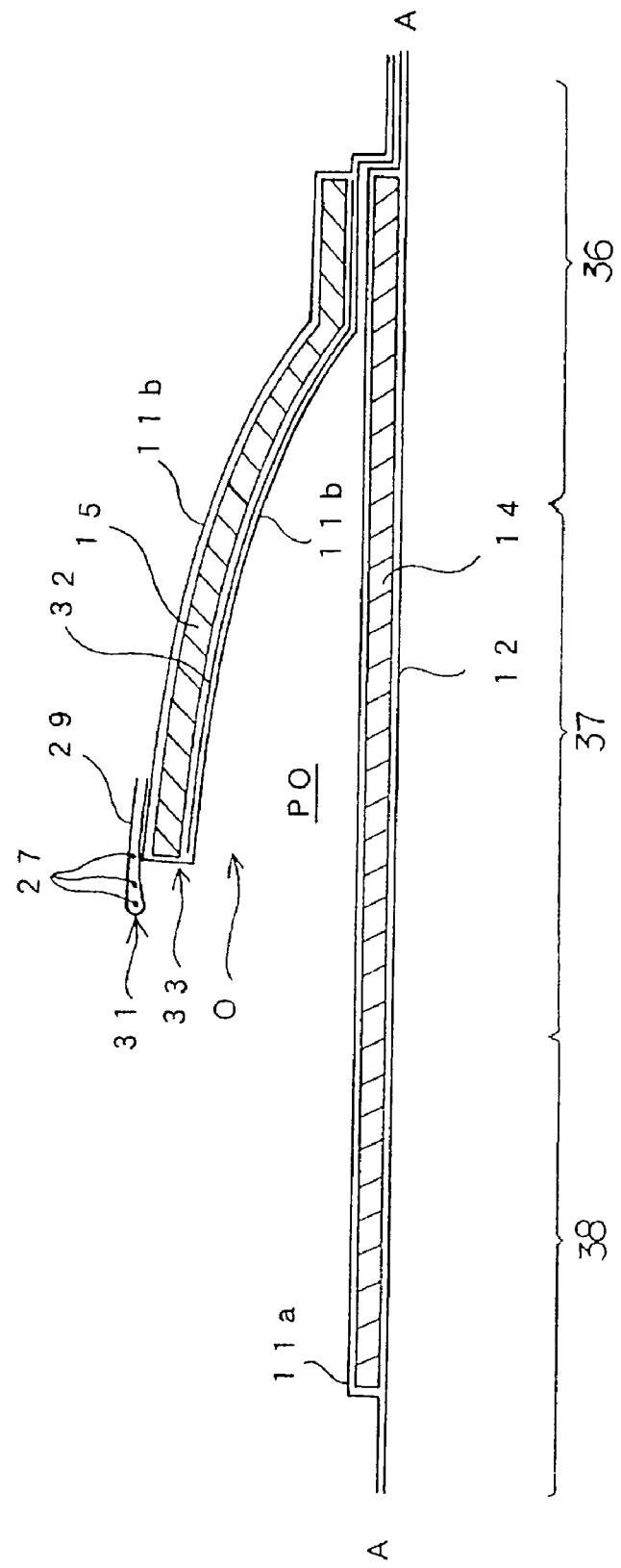
FIG. 4 is a section A-A' showing a modification of the development type paper diaper of the first mode of embodiment.

Here in the mode of embodiment thus far described, the top sheet 11 is so conformed to the shape of the pocket PO on the surfaces of the first absorbent 14 and the second absorbent 15 as to cover the leakage preventing sheet 32. However, this invention should not be limited thereto but may be modified such that the first absorbent 14 and the second absorbent 15 are separately covered with top sheets 11a and 11b, as shown in FIG. 4. On the back sheet 12, specifically, there is mounted the first absorbent 14, which is covered with the top sheet 11a. Over this top sheet 11a, there is placed the second absorbent 15 which is enveloped by the other top sheet 11b. On the second absorbent 15 on the side of the first absorbent 14, there is disposed the leakage preventing sheet 32, which is covered with the top sheet 11b. Moreover, the excrement containing gathering 31 is disposed at the opening upper end 33 on the top sheet 11b of the second absorbent 15 on the opposite side of the first absorbent 14.

If the development type paper diaper is thus formed, the top sheet 11 need not be conformed to the pocket PO, but the first absorbent 14 and the second absorbent 15 are covered with the top sheets 11a and 11b, respectively, to simplify the manufacturing process.

(Second Mode of Embodiment)

Figure 5:
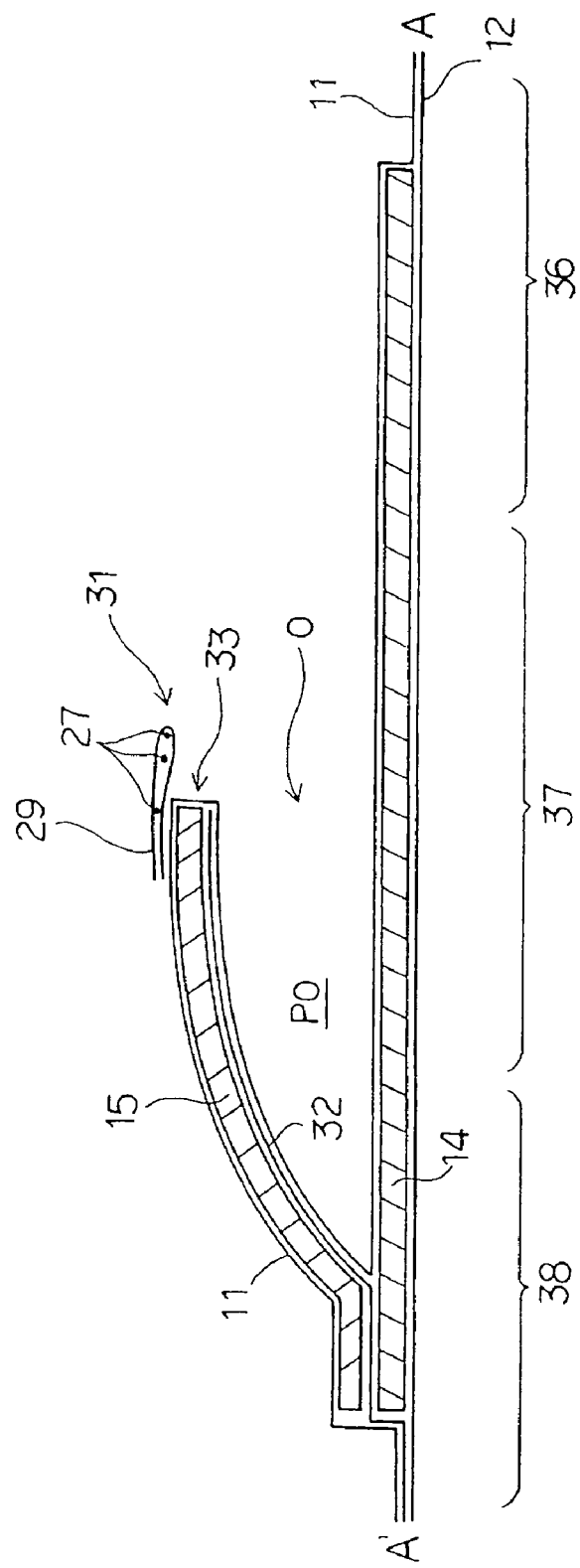
FIG. 5 is a section A-A' showing a development type paper diaper of a second mode of embodiment of this invention.

Next, a second mode of embodiment of this invention is described with reference to FIG. 5. This mode of embodiment is different from the first mode of embodiment in the disposition of the second absorbent 15 and in the direction of the pocket which is formed by the second absorbent 15 and the first absorbent. The remaining constitutions are similar to those of the first mode of embodiment so that their description is simplified.

The development type paper diaper of this mode of embodiment is provided with the back sheet 12, the first absorbent 14, the second absorbent 15 and the top sheet 11 in this recited order. The first absorbent 14 is disposed, when worn, to extend from the back side 36 through the crotch 37 to the abdomen side 38 of the user, and the second absorbent 15 is disposed, when worn, to extend from the crotch 37 to the abdomen side 38 of the user. The leakage preventing sheet 32 for allowing no liquid permeation is interposed between the first absorbent 14 and the second absorbent 15. The second absorbent 15 is spaced from the first absorbent 14 as it goes from the crotch 37 to the abdomen side 38 so that the pocket PO for holding the excrement is formed between the first absorbent 14 and the second absorbent 15. In that pocket PO, the leakage preventing sheet 32 is arranged to contact with the second absorbent 15, and the top sheet 11 is so conformed to the shape of the pocket PO as to cover the leakage preventing sheet 32.

Along the opening upper end 33 of the pocket PO, moreover, the excrement containing gathering 31 is adhered to the top sheet 11 over the second absorbent 15.

This excrement containing gathering 31 is provided with the three elastic members 27 along the widthwise direction a on the inner side by folding back the gathering sheet 29 formed of nonwoven fabric in the longitudinal direction b.

In this drawing, the excrement containing gathering 31 is provided with the three elastic members 27, to which the invention should not be limited.

(Third Mode of Embodiment)

Figure 6:
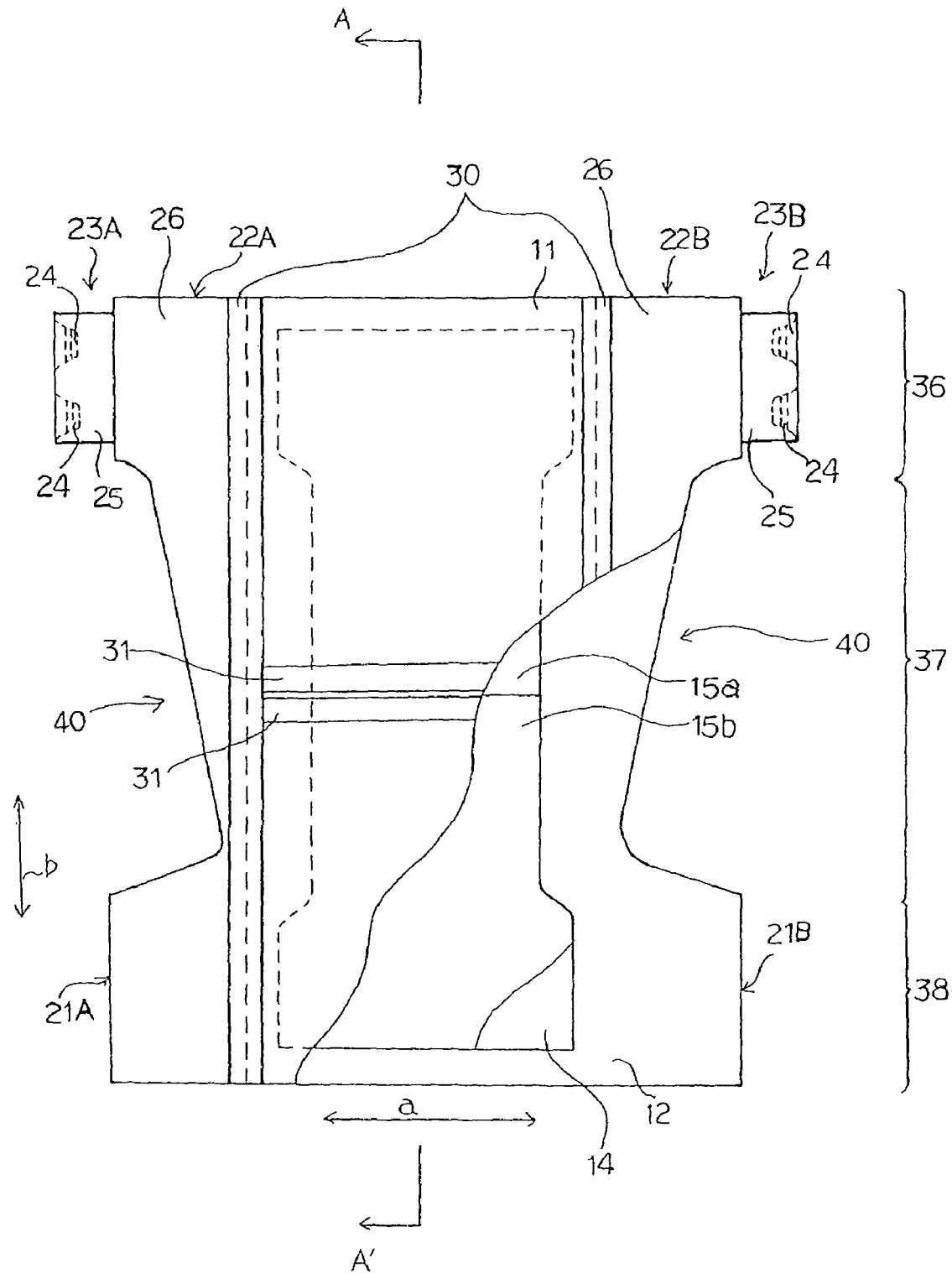
FIG. 6 is a top plan view of a development type paper diaper of a third mode of embodiment of this invention.
Figure 7:
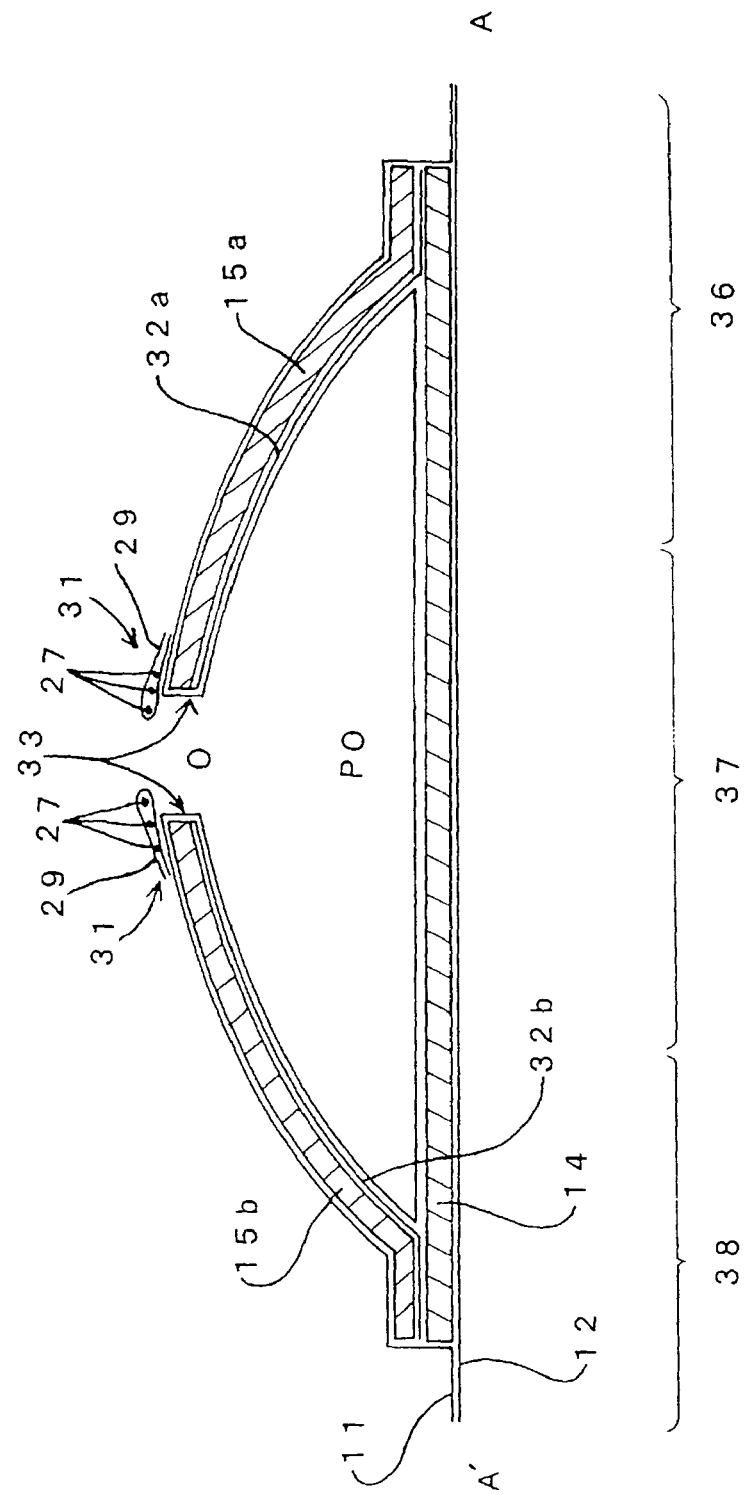
FIG. 7 is a section A-A' of the development type paper diaper of FIG. 7.

Next, a third mode of embodiment of this invention is described with reference to FIGS. 6 and 7. This mode of embodiment is different from the first and second modes of embodiment in that it is provided with two second absorbents, i.e., the back side second absorbent and the abdomen side second absorbent, and in the shape of the pocket PO. The remaining constitutions are similar to those of the first mode of embodiment so that their description is simplified.

The development type paper diaper of this mode of embodiment is provided with the back sheet 12, the first absorbent 14, a back side second absorbent (or a second absorbent) 15*a* and an abdomen side second absorbent (or a second absorbent) 15*b*, and the top sheet 11 in this recited order. The first absorbent 14 is disposed, when worn, to extend from the back side 36 through the crotch 37 to the abdomen side 38 of the user. The back side second absorbent 15*a* is disposed, when worn, to extend from the back side 36 to the crotch 37 of the user, and the abdomen side second absorbent 15*b* is disposed, when worn, to extend from the crotch 37 to the abdomen side 38 of the user. Leakage preventing sheets 32*a* and 32*b* for allowing no liquid permeation are interposed, respectively, between the first absorbent 14 and the back side second absorbent 15*a* and between the first absorbent 14 and the abdomen side second absorbent 15*b*. The back side second absorbent 15*a* is spaced from the first absorbent 14 as it goes from the crotch 37 to the back side 36, and the abdomen side second absorbent 15*b* is spaced from the first absorbent 14 as it goes from the crotch 37 to the abdomen side 38, so that the pockets PO for holding the excrement are formed individually between the first absorbent 14 and the back side second absorbent 15*a* and between the first absorbent 14 and the abdomen side second absorbent 15*b*. In those pockets PO, the leakage preventing sheet 32*a* and the leakage preventing sheet 32*b* are arranged to contact with the back side second absorbent 15*a* and the abdomen side second absorbent 15*b*, respectively. The top sheet 11 is so conformed to the shape of the pockets PO as to cover the leakage preventing sheets 32*a* and 32*b*.

Along the opening upper end 33 of the pocket PO, moreover, the excrement containing gathering 31 is adhered to each of the top sheets 11 over the back side second absorbent 15*a* and the abdomen side second absorbent 15*b*.

This excrement containing gathering 31 is provided with the three elastic members 27 along the widthwise direction a on the inner side by folding back the gathering sheet 29 formed of nonwoven fabric in the longitudinal direction b.

In this drawing, the excrement containing gathering 31 is provided with the three elastic members 27, to which the invention should not be limited.

(Fourth Mode of Embodiment)

Figure 8:
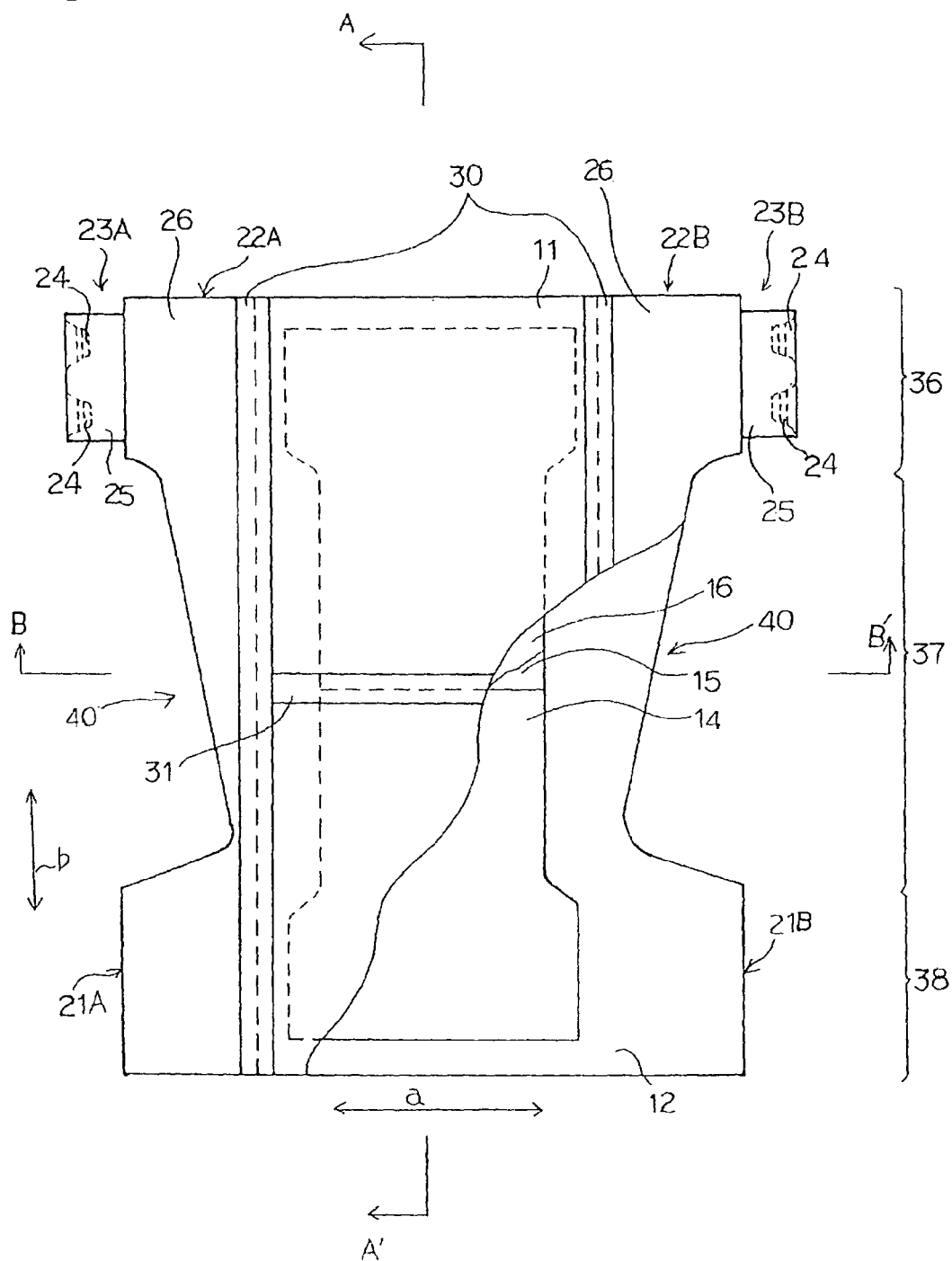
FIG. 8 is a top plan view of a development type paper diaper of a fourth mode of embodiment of this invention.
Figure 9:
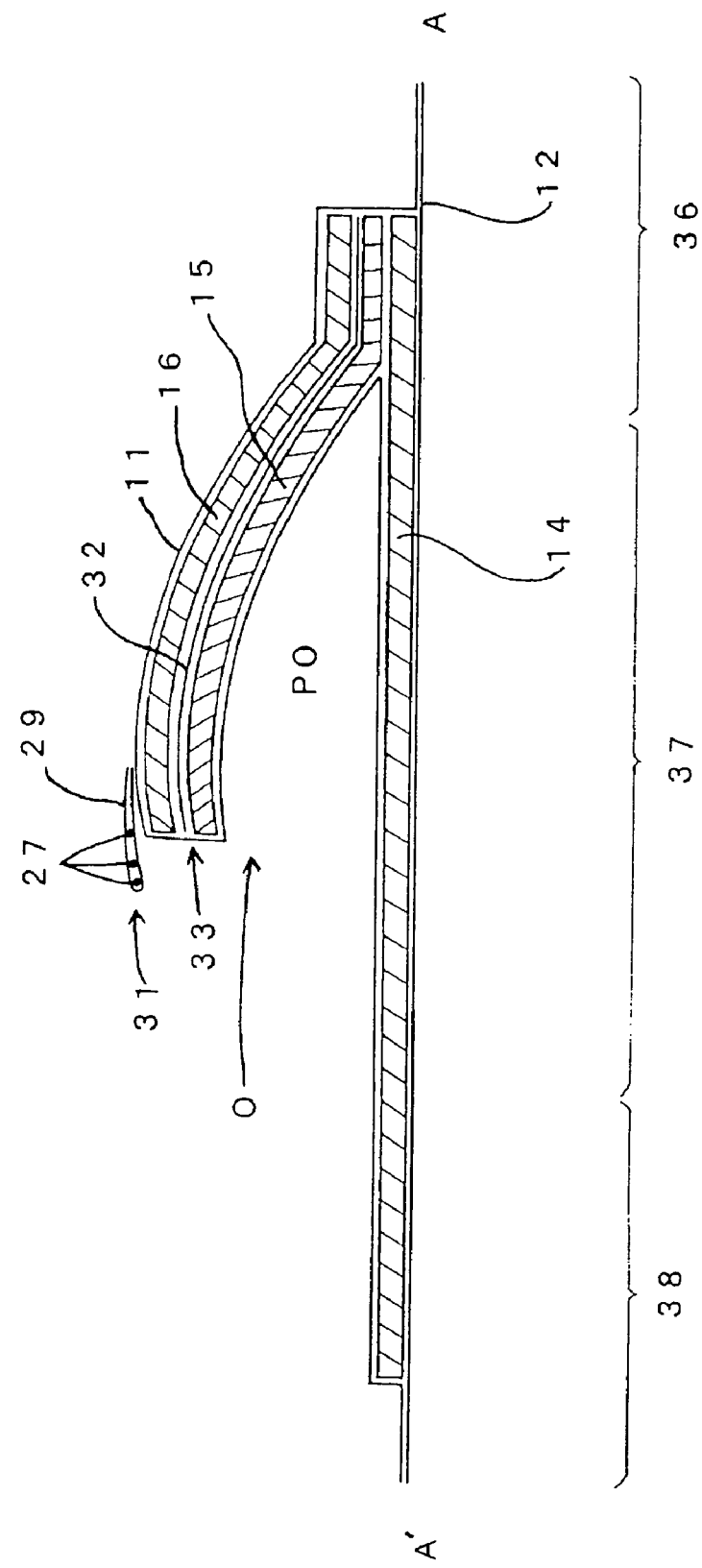
FIG. 9 is a section A-A' of the development type paper diaper of FIG. 8.
Figure 10:
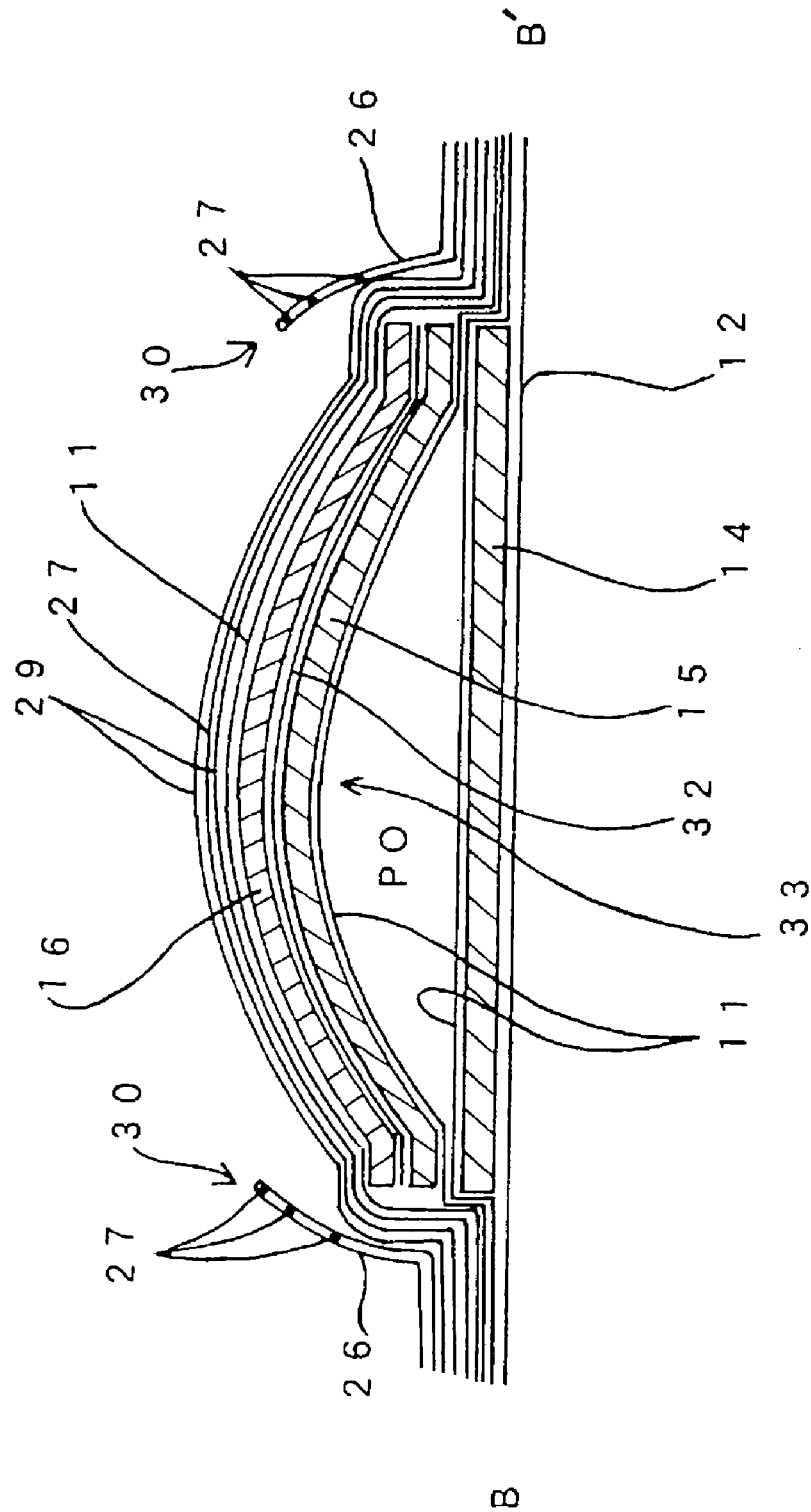
FIG. 10 is a section B-B' of the development type paper diaper of FIG. 8.

Next, a fourth mode of embodiment of this invention is described with reference to FIGS. 8, 9 and 10. This mode of embodiment is different from the first mode of embodiment in that the second absorbent 15 is provided with a third absorbent 16 through the leakage preventing sheet 32. The remaining constitutions are similar to those of the first mode of embodiment so that their description is simplified.

The development type paper diaper of this mode of embodiment is provided with the back sheet 12, the first absorbent (or a lower-layer absorbent) 14, the second absorbent (or an intermediate-layer absorbent) 15, a third absorbent (or an upper-layer absorbent) 16, and the top sheet 11 in this recited order. The first absorbent 14 is disposed, when worn, to extend from the back side 36 through the crotch 37 to the abdomen side 38 of the user, and the second absorbent 15 and the third absorbent 16 are disposed, when worn, to extend from the back side 36 to the crotch 37 of the user. The leakage preventing sheet 32 for allowing no liquid permeation is interposed between the second absorbent 15 and the third absorbent 16. The second absorbent 15 is spaced from the first absorbent 14 as it goes from the crotch 37 to the back side 36 so that the pocket PO for holding the excrement is formed between the first absorbent 14 and the second absorbent 15. Here, the top sheet 11 is conformed to the shape of the pocket PO. At this time, the second absorbent 15 is adhered at its peripheral edge portion other than the opening O to the first absorbent 14 by means of the hot-melt adhesive.

Along the opening O of the pocket PO, moreover, the excrement containing gathering 31 is disposed on the top sheet 11 of the third absorbent 16, and the cubic leg gathering 30 is disposed along the first absorbent 14.

In this drawing, the cubic leg gathering 30 and the excrement containing gathering 31 are individually provided with the three elastic members 27, to which the invention should not be limited.

When the development type paper diaper thus constituted is to be used, the user having face up lies at his or her buttocks on the top sheet 11 or the using face of the back side 36.

Then, the crotch 37 is applied to the crotch portion of the user, and the development type paper diaper is folded to place the abdomen side 38 on the abdomen of the user. The mechanical fasteners or the male members of the stopper portions 24 on the back side 36 are engaged with and fastened by the back sheet 12 of the abdomen side 38. Thus, the user wears the development type paper diaper. Then, the second absorbent 15 and the third absorbent 16 are raised to follow the body shape of the user by the excrement containing gathering 31 thereby to form the pocket PO.

If the excrement containing gathering 31 is closely worn on the vicinity of the sacrum portion of the user, the opening O of the pocket PO can catch the excrement of the user properly thereby to hold it easily in the pocket PO. If the amount of the pulp is made less at the center of the first absorbent 14 in the widthwise direction a than on the two sides in the widthwise direction a, the center of the first absorbent 14 in the widthwise direction a is more recessed than on the two sides so that the excrement can be gathered at the center and easily guided to the pocket PO.

Figure 11:
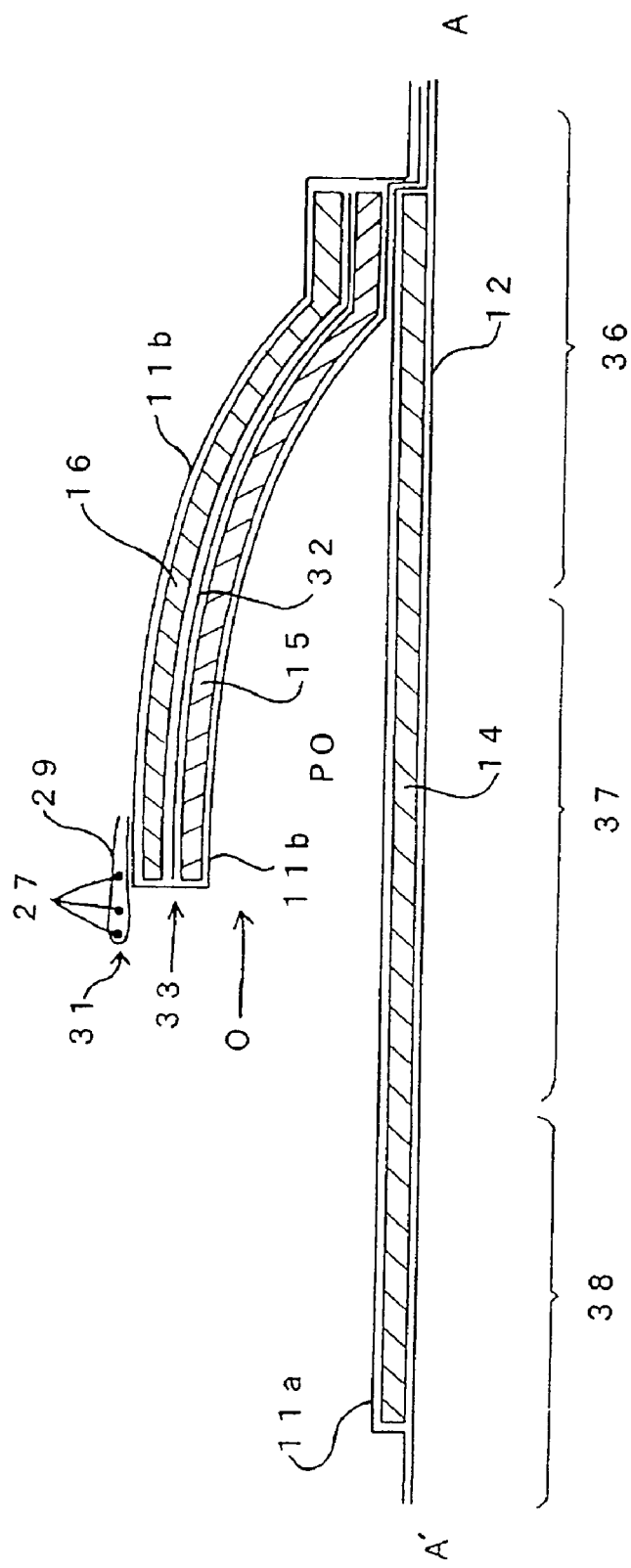
FIG. 11 is a section A-A' showing a modification of the development type paper diaper of the fourth mode of embodiment.

Here in this mode of embodiment thus far described, the top sheet 11 is so conformed to the shape of the pocket PO on the surfaces of the first absorbent 14, the second absorbent 15 and the third absorbent 16 as to cover the leakage preventing sheet 32. However, this invention should not be limited thereto but may be modified such that the first absorbent 14, the second absorbent 15 and the third absorbent 16 are separately covered with top sheets 11*a* and 11*b*, as shown in FIG. 11.

On the back sheet 12, specifically, there is mounted the first absorbent 14, which is covered with the top sheet 11*a*. Over this top sheet 11*a*, there are placed the second absorbent 15 and the third absorbent 16, which are enveloped by the other top sheet 11*b*. Here, the leakage preventing sheet 32 is interposed between the second absorbent 15 and the third absorbent 16. Moreover, the excrement containing gathering 31 is disposed at the opening upper end 33 on the top sheet 11*b* covering the third absorbent 16.

If the development type paper diaper is thus formed, the top sheet 11 need not be conformed to the pocket PO, but the first absorbent 14, the second absorbent 15 and the third absorbent 16 are covered with the top sheets 11*a* and 11*b*, respectively, to simplify the manufacturing process.

Moreover, the first absorbent 14 may be made of pulp in less amount at the center in the widthwise direction a than on the two sides of the widthwise direction a. With this arrangement, the center of the first absorbent 14 in the widthwise direction a is more recessed than on the two sides so that it can gather the excrement at the center and can guide it easily to the pocket PO thereby to keep the using face clean.

(Fifth Mode of Embodiment)

Figure 12:
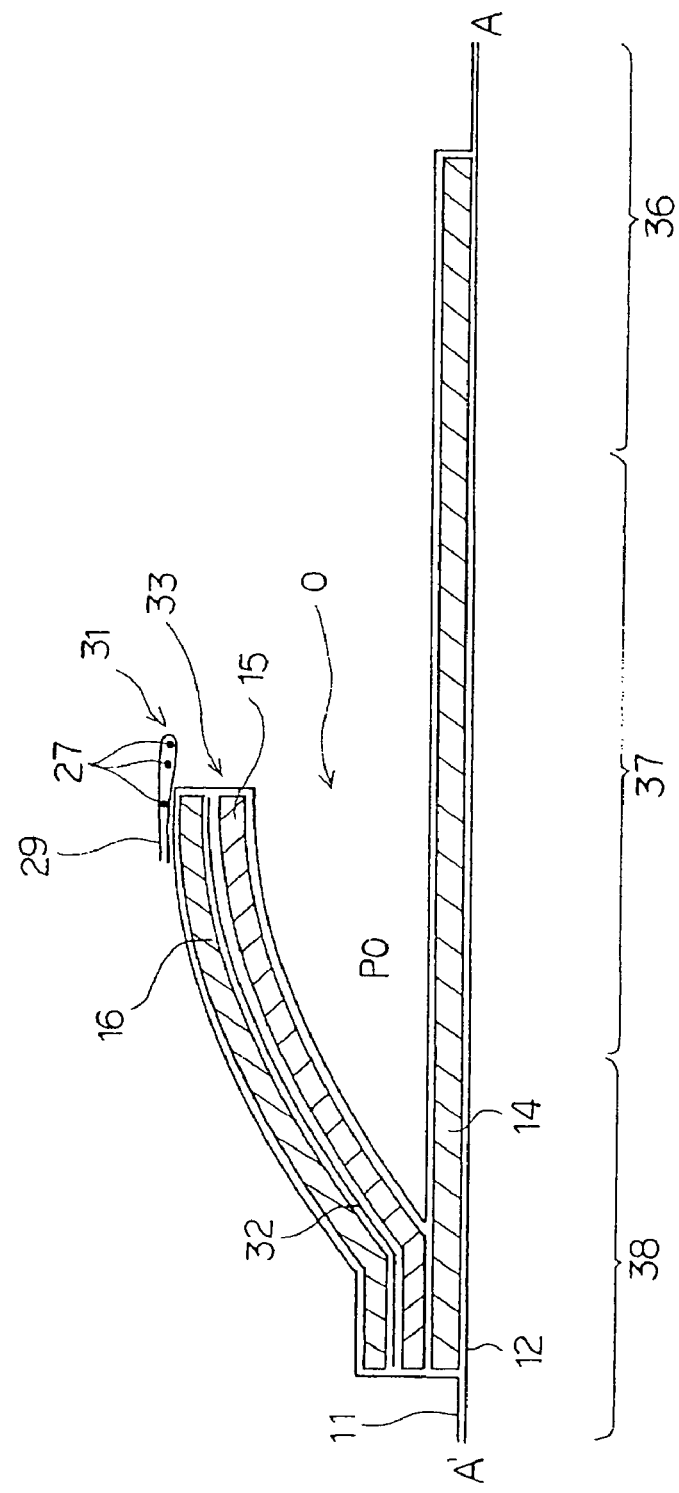
FIG. 12 is a section A-A' showing a development type paper diaper of a fifth mode of embodiment of this invention.

Next, a fifth mode of embodiment of this invention is described with reference to FIG. 12. This mode of embodiment is different from the fourth mode of embodiment in the disposition of the second absorbent 15 and in the direction of the pocket PO which is formed by the second absorbent 15 and the first absorbent. The remaining constitutions are similar to those of the first mode of embodiment so that their description is simplified.

The development type paper diaper of this mode of embodiment is provided with the back sheet 12, the first absorbent (or the lower-layer absorbent) 14, the second absorbent (the intermediate-layer absorbent) 15, the third absorbent (or the upper-layer absorbent) 16 and the top sheet 11 in this recited order. The first absorbent 14 is disposed, when worn, to extend from the back side 36 through the crotch 37 to the abdomen side 38 of the user, and the second absorbent 15 and the third absorbent 16 are disposed, when worn, to extend from the crotch 37 to the abdomen side 38 of the user. Moreover, the leakage preventing sheet 32 for allowing no liquid permeation is interposed between the second absorbent 15 and the third absorbent 16. The second absorbent 15 is spaced from the first absorbent 14 as it goes from the crotch 37 to the abdomen side 38 so that the pocket PO for holding the excrement is formed between the first absorbent 14 and the second absorbent 15. Here, the top sheet 11 is conformed to the shape of the pocket PO.

Along the opening upper end 33 of the pocket PO, moreover, the excrement containing gathering 31 is adhered to the top sheet 11 over the third absorbent 16.

This excrement containing gathering 31 is provided with the three elastic members 27 along the widthwise direction a on the inner side by folding back the gathering sheet 29 formed of nonwoven fabric in the longitudinal direction b.

In this drawing, the excrement containing gathering 31 is provided with the three elastic members 27, to which the invention should not be limited.

(Sixth Mode of Embodiment)

Figure 13:
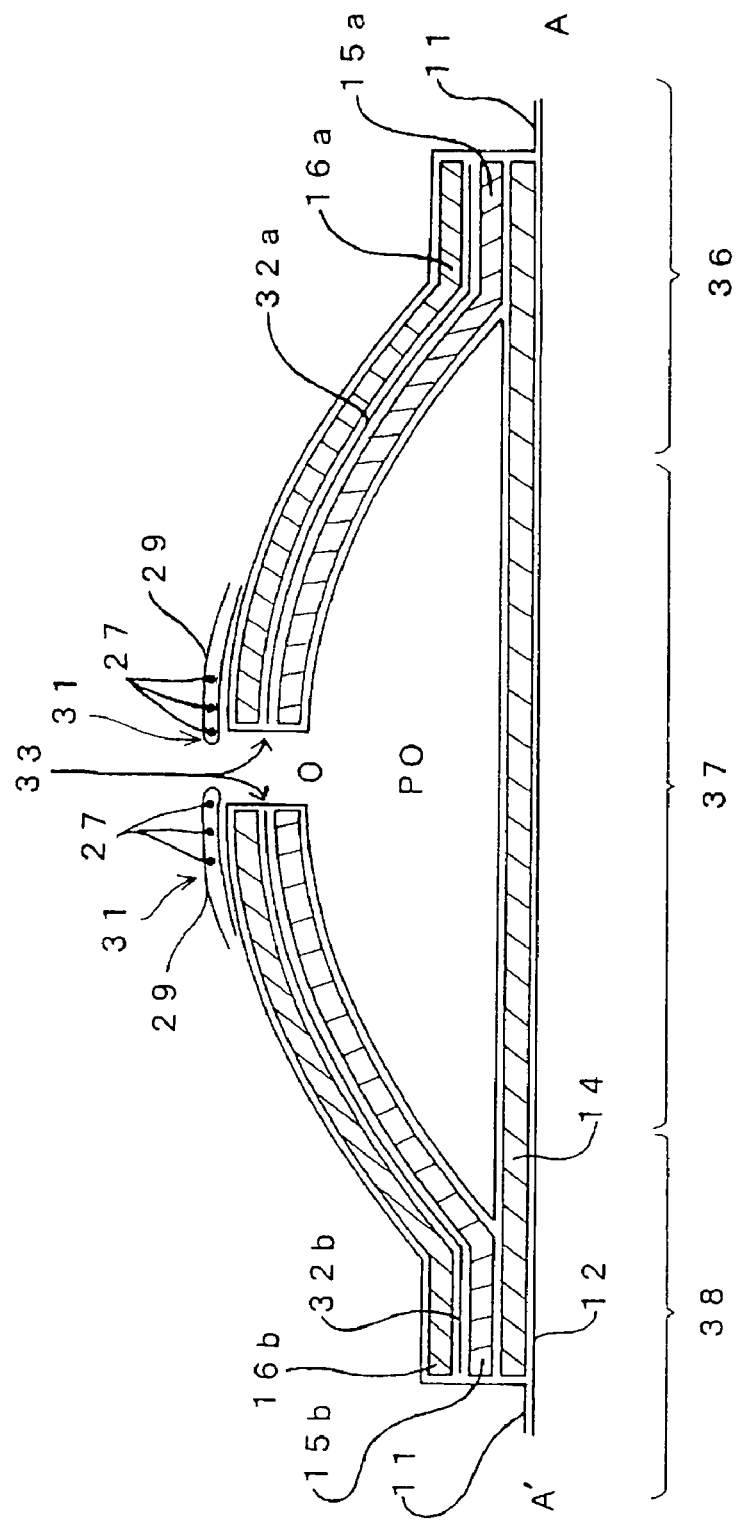
FIG. 13 is a section A-A' showing a development type paper diaper of a sixth mode of embodiment of this invention.
Figure 14:
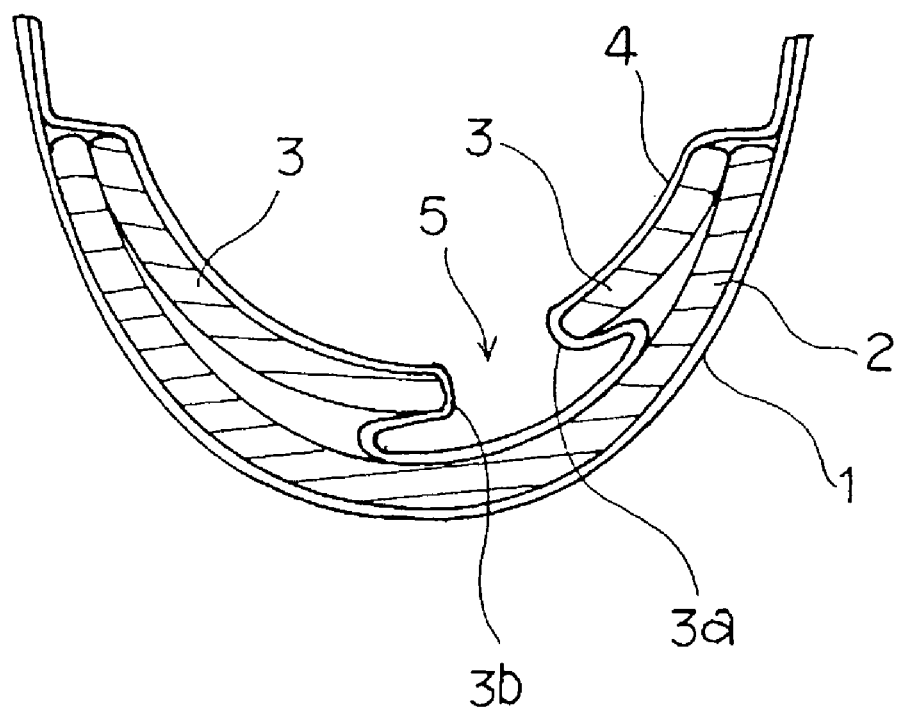
FIG. 14 is a section of a development type paper diaper of the prior art.

Next, a sixth mode of embodiment of this invention is described with reference to FIG. 13. This mode of embodiment is different from the fourth and fifth modes of embodiment in that two second absorbents are disposed as the back side second absorbent and the abdomen side second absorbent, in that two third absorbents are disposed as the back side absorbent and the abdomen side third absorbent, and in the shape of the pocket PO. The remaining constitutions are similar to those of the fourth and fifth modes of embodiment so that their description is simplified.

The development type paper diaper of this mode of embodiment is provided with the back sheet 12, the first absorbent (or the lower-layer absorbent) 14, the second absorbent or the back side second absorbent (the intermediate-layer absorbent) 15*a*, the third absorbent having the same shape as that of that back side second absorbent 15*a* or a back side third absorbent (or the upper-layer absorbent) 16*a*, the second absorbent or the abdomen side second absorbent (the intermediate-layer absorbent) 15*b*, the third absorbent having the same shape as that of that abdomen side second absorbent 15*b* or an abdomen side third absorbent (or the upper-layer absorbent) 16*b*, and the top sheet 11 in this recited order.

The first absorbent 14 is disposed, when worn, to extend from the back side 36 through the crotch 37 to the abdomen side 38 of the user. The back side second absorbent 15*a* and the back side third absorbent 16*a* are disposed, when worn, to extend from the back side 36 to the crotch 37 of the user, and the abdomen side second absorbent 15*b* and the abdomen side third absorbent 16*b* are disposed, when worn, to extend from the crotch 37 to the abdomen side 38 of the user. Moreover, the leakage preventing sheets 32*a* and 32*b* for allowing no liquid permeation are interposed, respectively, between the back side second absorbent 15*a* and the back side third absorbent 16*a* and between the abdomen side second absorbent 15*b* and the abdomen side third absorbent 16*b*.

Moreover, the back side second absorbent 15*a* is spaced from the first absorbent 14 as it goes from the crotch 37 to the back side 36, and the abdomen side second absorbent 15*b* is spaced from the first absorbent 14 as it goes from the crotch 37 to the abdomen side 38 so that the pockets PO for holding the excrement are formed individually between the first absorbent 14 and the back side second absorbent 15*a* and between the first absorbent 14 and the abdomen side second absorbent 15*b*. Here, the top sheet 11 is conformed to the shape of the pockets PO.

Along the opening upper end 33 of the pocket PO, moreover, the excrement containing gathering 31 is adhered to the top sheet 11 over each of the back side second absorbent 15*a* and the abdomen side second absorbent 15*b*.

This excrement containing gathering 31 is provided with the three elastic members 27 along the widthwise direction a on the inner side by folding back the gathering sheet 29 formed of nonwoven fabric in the longitudinal direction b.

In this drawing, the excrement containing gathering 31 is provided with the three elastic members 27, to which the invention should not be limited.

The top sheet 11 to be employed in the invention is a liquid permeable nonwoven or woven fabric or a porous plastic film. This fabric or film is formed of single fibers of polypropylene, polyethylene, polyester or nylon or the like, or conjugate fibers composed of two or more of polyester, polypropylene, polyethylene nylon, or the like. Especially, the conjugate fibers of polyester/polyester, polyester/polyethylene or polypropylene/polyethylene are preferable for the strength, but are not limited. Alternatively, the top sheet may also be formed of a liquid permeable nonwoven fabric.

The back sheet 12 and the panel base 25 to be employed in the invention are made of a material such as a liquid-impermeable film of PE (polyethylene) or an adhesion of a liquid-impermeable film and a nonwoven or woven fabric. In case the liquid-impermeable film is employed, a polyethylene film having such numerous pores as to inhibit the liquid permeation, a moisture permeable film stretched from a thermoplastic resin by adding a filler, or a composite sheet having a nonwoven or woven fabric adhered to one of those films is used to prevent stuffiness. Then, the excessive moisture in an absorbent pad is released in the gaseous state to the outside so that the stuffiness or rash becomes hard to occur thereby to make the composite sheet comfortable in moisture permeability and skin touch. Here, the back sheet 12 may also be made of a liquid-permeable material such as the nonwoven fabric.

The first absorbent 14, the second absorbents 15, 15a and 15b and the third absorbents 16, 16a and 16b to be employed in the invention are made of cotton-yarn pulp, a super absorptive polymer (as will be called the "SAP") or a hydrophilic sheet, although not especially limitative. Moreover, the absorbent to be employed in the invention is made of the well-known absorptive material which is usually used in the development type paper diaper of the prior art or other absorbent articles.

Specifically, either the single- or multi-layer mat, in which absorptive fibers of cotton-yarn pulp or rayon and the SAP are mixed, or the homogeneous arrangement, in which the SAP is homogeneously arranged between the layers of mats of absorptive fibers, may be wrapped with a hydrophilic sheet.

The cotton-yarn pulp to be used can be prepared by opening a chemical pulp sheet or a mechanical pulp sheet by a grinder. The pulp material may be not only soft wood pulp but also hard wood pulp, straw, bamboo or kenaf. Alternatively, waste paper pulp may also be used. The amount of this cotton-yarn pulp is generally exemplified by 50 to 600 $g/m^2$, although different for the target absorbent such as for a single use or a laminated use or a combined use with another absorbent.

The SAP is exemplified by a starch group, a cellulose group or a synthetic polymer group. Specifically, the usable ones are: graft copolymers of starch-acrylic acid (or salt) saponified copolymer of starch-acrylate ethyl graft; saponified copolymer of starch-metacrylate methyl graft; saponified copolymer of starch-acrylonitrile graft; saponified copolymer of starch-acrylamide graft; copolymer of acrylic acid (or acrylate); polyethylene oxide crosslinked with acrylic acid; crosslinked sodium carboxy methyl cellulose; and crosslinked reactants of polyvinyl alcohol-maleic anhydride.

The first absorbent 14, the second absorbents 15, 15a and 15b and the third absorbents 16, 16a and 16b may be compressed by a roll having a smooth circumference into such a continuous place, in which the densities of the absorbents are substantially equal all over. Alternatively, a roll having undulating circumference may also be used to compress those absorbents to form embosses, in which the densities are so partially different as to guide the urine or humor longitudinally or obliquely. In the emboss case, the compressed portions or the uncompressed portions may be either continuous or discontinuous.

The gathering sheet 26 or the gathering sheet 29 to be used in the invention may be made of the water-proofed nonwoven or woven fabric, a liquid-impermeable film of polyethylene, or a material prepared by adhering that liquid-impermeable film and the nonwoven or woven fabric. In case the liquid-impermeable film is used, the preferred one is the polyethylene film which has a number of such pores as will not permeate the liquid molecules so as to prevent the stuffiness, or the moisture-permeable film which is stretched by adding the filler to a thermoplastic resin.

In case the nonwoven or woven fabric is used, the component fibers have the well-known component of the PP (polypropylene), PE, polyester, PET or nylon. Of these, the PET or PP is preferred for its high strength. Of the single layer and the two layers and the three or more layers, the two or more layers are preferred for the high strength. The kinds to be used are the air-through, the point bond, the resin bond, the spun bond, the SMS and the SMMS, and among those the spun bond is preferred for the high strength. The amount preferred is 50 to 70 $g/m^2$ for the optimum stiffness.

The elastic member 27 to be used in the cubic gathering 30 and the excrement containing gathering 31 can be exemplified by the ordinary male absorbent pads made of natural or synthetic rubber or urethane and having a thread, string, net or flat shape, or an extensible elastomer used in the ordinary absorbent article. The extensible elastomer is arranged in an extended state and is adhered and fixed to the water-repellent material by the hot-melt, the water-soluble glue such as the starch or CMC (carboxy methyl cellulose), a highly fluid adhesive, or a welding with heat or ultrasonic waves.

The invention claimed is:

1. A development type paper diaper adapted to be worn on a human body for absorbing and holding excrement, comprising a back sheet, a first absorbent, a leakage preventing sheet allowing no liquid permeation, a second absorbent and a top sheet providing a body contact surface in the recited order, wherein said first absorbent extends, when worn, from the back side through the crotch to the abdomen side of the user and said second absorbent extends, when worn, from the back side to the crotch of the user, said second absorbent leaves said first absorbent from said crotch to said back side thereby to form a pocket for holding the excrement between said first absorbent and said second absorbent, said leakage preventing sheet, when viewed in section along a longitudinal axis of the diaper, extends from a terminal end thereof positioned substantially at a midpoint of the crotch of the user to the back side of the user and is arranged to contact in said pocket with said second absorbent therealong the entire length of the leakage preventing sheet that is contactable with the second absorbent throughout the entirety of said pocket, and said top sheet, when viewed in section along a longitudinal axis of the diaper, is so conformed to the shape of said pocket so as to follow an outline of the pocket throughout the entirety of said pocket in order to cover said leakage preventing sheet and to cover said first absorbent, said leakage preventing sheet and said second absorbent, throughout said outline of said pocket and within said pocket on top and bottom sides of said pocket so as to conform to the shape of said pocket between said top and bottom sides of said pocket, and exit said pocket so as to continue toward said abdomen side of the user.

2. A development type paper diaper as set forth in claim 1, wherein an excrement containing gathering is disposed along the opening upper end of said pocket and on said top sheet of said second absorbent.

3. A development type paper diaper as set forth in claim 1, wherein a cubic leg gathering is disposed along said first absorbent.

4. A development type paper diaper as set forth in claim 1, wherein said first absorbent comprises pulp and is formed of a lesser amount thereof at a widthwise center than on two opposing sides in a widthwise direction.

* * * * *